United States Patent [19]

Nohda

[11] 4,322,137

[45] Mar. 30, 1982

[54] FUNDUS OBSERVATION AND PHOTOGRAPHING OPTICAL SYSTEM

[75] Inventor: Masao Nohda, Yokohama, Japan

[73] Assignee: Nippon Kogaku K.K., Tokyo, Japan

[21] Appl. No.: 105,669

[22] Filed: Dec. 20, 1979

[30] Foreign Application Priority Data

Dec. 29, 1978 [JP] Japan .................................. 53-163082

[51] Int. Cl.$^3$ .......................... A61B 3/14; G03B 29/00
[52] U.S. Cl. ............................................ 351/7; 354/62
[58] Field of Search ........................... 351/7, 6; 354/62

[56] References Cited

U.S. PATENT DOCUMENTS

| | | | |
|---|---|---|---|
| 3,914,032 | 10/1975 | Takano et al. ............................ | 351/7 |
| 3,915,564 | 10/1975 | Urban ........................................ | 351/7 |
| 4,098,549 | 7/1978 | Matsumura .............................. | 351/7 |
| 4,222,634 | 9/1980 | Muchel ................................. | 351/7 X |

*Primary Examiner*—John K. Corbin
*Assistant Examiner*—Rodney Bovernick
*Attorney, Agent, or Firm*—Fitzpatrick, Cella, Harper & Scinto

[57] ABSTRACT

In a fundus observation and photographing optical system having an objective lens for forming a primary image of the fundus of an eye to be examined, an apertured mirror disposed rearwardly of the objective lens and obliquely with respect to the optic axis of the lens and having an opening on the optic axis, an illuminating optical system for supplying illuminating light to the eye via the apertured mirror and through the objective lens, and an image forming relay lens for forming a secondary image from said primary image, the objective lens has, in succession from the side of the eye, a first group comprising a biconvex lens having its more sharply convex surface facing the apertured mirror, and a second group comprising a doublet of a biconvex lens and a biconcave lens and having its concave surface facing the apertured mirror.

12 Claims, 5 Drawing Figures

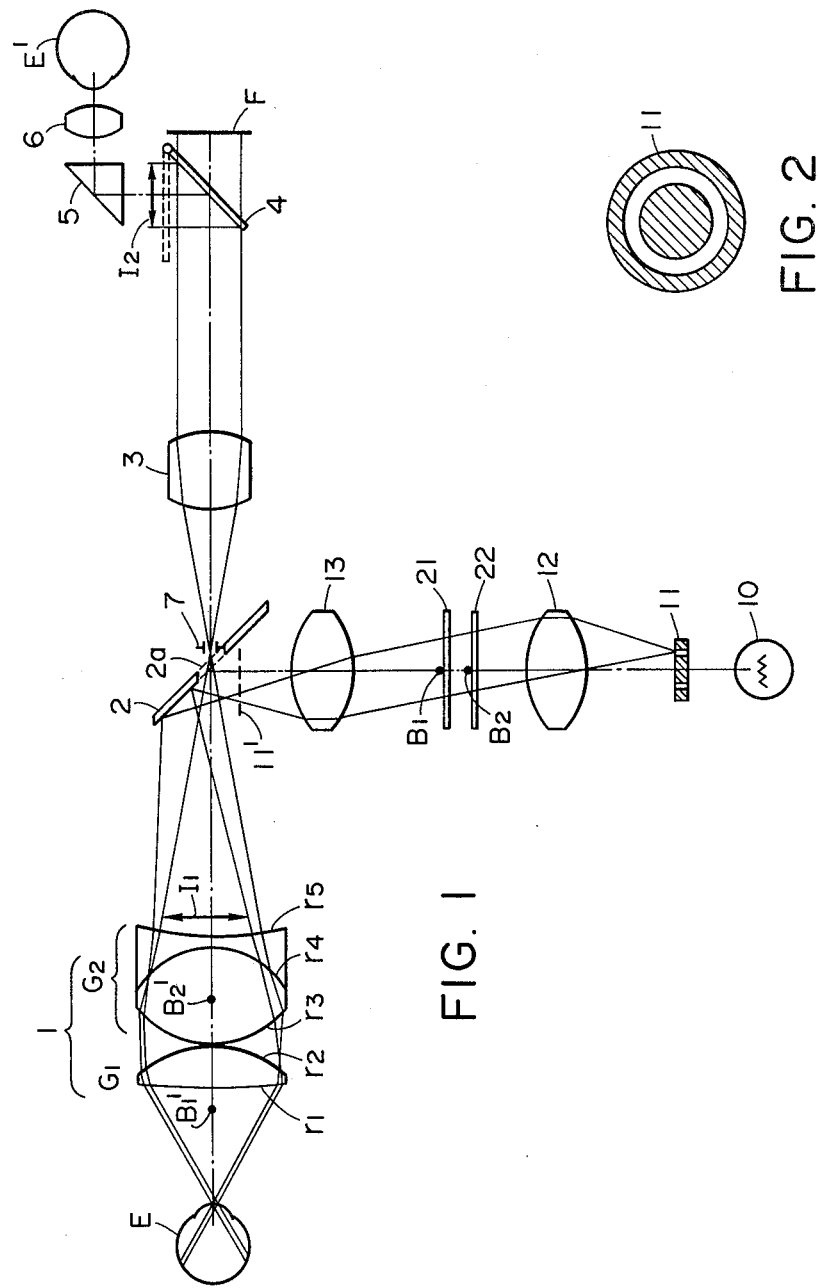

FUNDUS OBSERVATION AND PHOTOGRAPHING OPTICAL SYSTEM

BACKGROUND OF THE INVENTION

1. Field of the invention

This invention relates to an optical system such as retinal camera, and particularly the objective lens thereof, for observing or photographing therethrough the fundus.

2. Description of the Prior Art

A lens having a wide angle of view which can form an image of a wide range of the fundus is desired as the objective lens of a retinal camera. However, since the reflection factor of the fundus is originally small, the reflected light on each surface of the lens must be sufficiently eliminated and it has been very difficult to construct a lens having a wide angle of view and yet having an excellent image forming performance. Various wide angle objective lenses of such type have heretofore been proposed but their angle of view has only been 45° to 50° at best.

SUMMARY OF THE INVENTION

It is the object of the present invention to provide a fundus observation and photographing optical system having an objective lens having a wide angle of view and an excellent image forming performance and more specifically, to provide an objective lens having an angle of view of 60°.

Generally, in fundus observation and photographing devices, the objective lens is provided between an eye to be examined and an obliquely disposed apertured mirror for directing illuminating light to the eye to be examined. Observation and photographing of the fundus are effected through the opening of the apertured mirror and as is well-known, this opening performs the function of a diaphragm for eliminating the illuminating light reflected from each lens surface of the objective lens. The fundus observation and photographing optical system according to the present invention is used in a condition substantially similar to that of the conventional device, and the characteristic objective lens of the present invention basically comprises the following two groups. That is, in succession from the side of the eye to be examined, a first group comprising a biconvex lens having its more sharply convex surface facing the apertured mirror, and a second group comprising a doublet of a biconvex lens and a biconcave lens and having its concave surface facing the apertured mirror. The eye to be examined and the apertured mirror are disposed at positions substantially conjugate with this objective lens, and a first, a second and a third surface of the objective lens as counted from the side of said eye have convergent refractive power, a fourth surface of the objective lens has divergent refractive power and moreover, the center of curvature of a fifth surface which is the last surface of the objective lens lies substantially at the position of the apertured mirror.

The invention will become more fully apparent from the following detailed description thereof taken in conjunction with the accompanying drawings.

BRIEF DESCRIPTION OF THE DRAWINGS

FIG. 1 is a schematic cross-sectional view of the optical system of a retinal camera using the objective lens according to the present invention.

FIG. 2 is a plan view of a ring slit.

DESCRIPTION OF THE PREFERRED EMBODIMENTS

Figure 3:
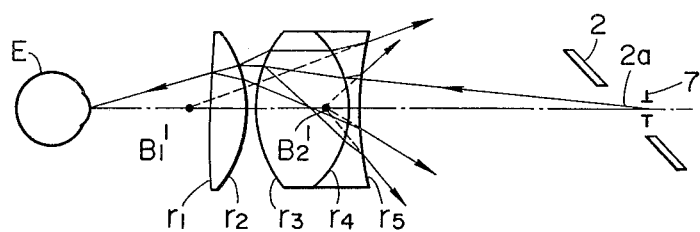
FIG. 3 illustrates the objective lens of FIG. 1.

The invention will hereinafter be described with respect to an embodiment thereof. FIG. 1 is a schematic cross-sectional view of the optical system of a retinal camera using the objective lens according to the present invention.

The objective lens 1 of the present invention comprising a first group $G_1$ and a second group $G_2$ is provided between an eye E to be examined and an obliquely disposed apertured mirror 2, and the cornea of the eye to be examined and the opening 2a of the apertured mirror are substantially conjugate with respect to the objective lens 1. A first space image $I_1$ of the fundus of the eye to be examined is formed between the objective lens 1 and the apertured mirror 2. The light passed through the opening 2a of the apertured mirror 2 is condensed by an image forming relay lens 3 and reflected by a pivotable mirror 4, whereafter it forms a second space image $I_2$ of the fundus of the eye to be examined, and this second space image is observed by the examiner's eye E' through a prism 5 and an eyepiece 6. When the mirror 4 is pivoted to the outside of the light path as indicated by dotted line in FIG. 1, the light from the image forming relay lens 3 reaches a film surface F, whereby photography of the fundus is effected. On the other hand, the light from a light source 10 illuminates a ring slit 11 having a ring-shaped opening as shown in the plan view of FIG. 2, and the image 11' of the ring slit 11 is formed in the vicinity of the apertured mirror 2 by a first relay lens 12 and a second relay lens 13. This image 11' of the ring slit is reflected by the apertured mirror and projected upon the cornea of the eye to be examined by the objective lens 1, and provides the fundus illuminating light. An observation opening 7 disposed immediately rearwardly of the apertured mirror 2 is for enhancing the stop effect provided by the opening 2a of the apertured mirror 2 and it is strictly this observation opening 7 that is conjugate with the cornea of the eye to be examined with respect to the objective lens 1.

A transparent first black point plate 21 having a first black point $B_1$ and a transparent second black point plate 22 having a second black point $B_2$ are disposed between the first relay lens 12 and the second relay lens 13, and the black points are projected at predetermined positions of the objective lens by the second relay lens 13 and the apertured mirror. That is, the image $B_1'$ of the first black point $B_1$ is formed at a position of the first group $G_1$ of the objective lens 1 which is slightly toward the eye to be examined, and the image $B_2'$ of the second black point $B_2$ is formed within a biconvex lens which is the second group of the objective group. Now, it is assumed that the lens surfaces of the objective lens 1 are $r_1$, $r_2$, $r_3$, $r_4$ and $r_5$ in the order from the eye to be examined, and description will be made of the light ray entering the objective lens 1 through the opening 2a of the apertured mirror 2, strictly the observation opening 7, and reflected by each refracting surface of the objective lens. The virtual image of the opening 2a is formed on the first black point image $B_1'$ by the light ray reflected by the second lens surface r₂. The size of this first black point image is as large as the virtual image of the opening 2a formed there. The light ray reflected by the first lens surface r₁ is refracted by the second lens surface r₂, the third lens surface r₃, the fourth lens surface r₄ and the fifth lens surface r₅, whereafter it forms the image of the opening 2a on the second black point image B₂', and the light ray reflected by the third lens surface r₃ is refracted by the fourth lens surface r₄ and the fifth lens surface r₅, whereafter it forms the image of the opening 2a on the second black point image B₂', and the light ray reflected by the fourth lens surface r₄ is refracted by the fifth lens surface r₅, whereafter it forms the image of the opening 2a on the second black point image B₂'. That is, the images of the opening 2a by the light rays reflected by the first lens surface, the third lens surface and the fourth lens surface, respectively, are formed at the position of the second black point image B₂', and the size of the second black point image B₂' is in accord with the size of the image of the opening 2a by the first lens surface r₁ which is the largest of the images of the opening 2a by the light rays reflected by the first, third and fourth lens surfaces. Therefore, of the illuminating light supplied through the ring slit 11 or supplied substantially through the opening 2a of the apertured mirror 2, the light rays reflected by the first to fourth lens surfaces and trying to pass through the opening 2a of the apertured mirror 2 are all absorbed and intercepted by the two black point images B₁' and B₂'.

Also, the center of curvature of the last lens surface r₅ lies in the opening 2a of the apertured mirror 2, strictly the observation opening 7, and therefore, of the ring-shaped light beam as the illuminating light, the light reflected by the last lens surface r₅ becomes an entirely similar ring-shaped light beam and does not pass through the opening 2a. That is, the reflected light from each lens surface is all eliminated and creates no flare in the image of the fundus, thus enabling a clear image to be observed and photographed.

An example of the numerical data of the objective lens according to the present invention will be shown below. In the list below, r₁, r₂, r₃, . . . represent the curvature radii of the respective lens surfaces in succession from the eye to be examined, d₁, d₂, d₃, . . . represent the center thicknesses of and the air spaces between the successive lenses, and nd and vd represent the refractive indices and Abbe numbers, respectively, of the successive lenses.

$$
\begin{array}{c}
G_1 \left\{ \begin{array}{l} r_1 = 380.0 \quad d_1 = 14.0 \quad nd_1 = 1.62041 \quad vd_1 = 60.3 \\ r_2 = -38.0 \quad d_2 = 0.5 \end{array} \right. \\
G_2 \left\{ \begin{array}{l} r_3 = 33.8 \quad d_3 = 32.6 \quad nd_2 = 1.62041 \quad vd_2 = 60.3 \\ r_4 = -30.0 \quad d_4 = 2.0 \quad nd_3 = 1.75520 \quad vd_3 = 27.5 \\ r_5 = 98.5 \end{array} \right.
\end{array}
$$

Total focal length f = 30.5 (unit: mm)

The third lens surface r₃ is formed into an aspherical surface in which spherical aberration is best corrected under the condition that the cornea of the eye to be examined and the opening 2a of the apertured mirror are conjugate with respect to this objective lens, and the above-shown value of r₃ represents the curvature radius of the standard spherical surface thereof.

Figure 4:
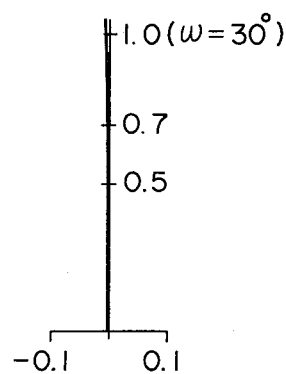
FIG. 4 shows the spherical aberration in the objective lens.
Figure 5:
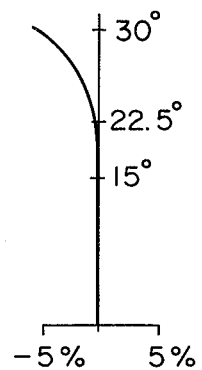
FIG. 5 shows the distortion of the fundus image formed by the objective lens.

The spherical aberration on pupil in the conjugate relation between the cornea of the eye to be examined and the apertured mirror with respect to this objective lens is shown in FIG. 4, and the distortion of the fundus image by the objective lens is shown in FIG. 5.

When the angle of view becomes 60°, it is very difficult to correct the spherical aberration and even in a conventional lens having an angle of view on the order of 45°, two aspherical surfaces have unavoidably been adopted, but in the present invention, only one surface is made into an aspherical surface to correct the spherical aberration very well as shown. Also, the distortion is substantially zero in the conventional angle of view of 45° (half angle of view 22.5°), as shown, and is well corrected even in the angle of view of 60° (half angle of view 30°).

In such objective lens according to the present invention, it is desirable that the following conditions be satisfied regarding the curvature radii r₂ and r₃ of the second and third lens surfaces.

$$0.7f < |r_2| < 2.0f$$

$$0.6f < |r_3| < 2.0f$$

where f represents the total focal length of the objective lens.

If the lower limits of the above two conditions are exceeded, the curvature radius of each lens surface will become too small and the edge thickness of the lens will become small, so that it will become difficult to obtain an aperture sufficient to receive light rays having a great angle of view. On the other hand, if the upper limits of the above two conditions are exceeded, the refractive power of each lens surface will become small and the black point image which should be conjugate with the opening of the apertured mirror will become large to more and more reduce the weak reflected light from the fundus.

If the curvature radius of the third lens surface r₃ is determined as described above, the black point which becomes conjugate with the opening of the apertured mirror with respect to the third lens surface is also conjugate with the opening of the apertured mirror with respect to the first and fourth lens surfaces and from this, the curvature radii of the first and fourth lens surfaces are substantially determined. Also, the curvature radius of the fifth lens surface which is the last lens surface is primarily determined from the positional relationship between the objective lens and the apertured mirror, as already described.

According to the present invention, as hitherto described, there is achieved a fundus observation and photographing optical system having an angle of view as wide as 60° and from which flare light is sufficiently eliminated, as well as having an excellent image forming performance. Moreover, the objective lens thereof is of a very simple construction which comprises three lenses of two groups with only one lens surface being aspherical, and this is very useful.

What we claim:

1. A fundus observation and photographing optical system having an objective lens for forming a primary image of the fundus of an eye to be examined, an apertured mirror disposed rearwardly of said objective lens and obliquely with respect to the optic axis of said objective lens and having an opening on the optic axis, said mirror being substantially conjugate with the cornea of said eye with respect to said objective lens during the observation or photographing of the fundus, an illuminating optical system having a light source and a first and a second relay lens, said illuminating optical system being adapted to supply illuminating light to said eye via said apertured mirror and through said objective lens, and an image forming relay lens for forming a secondary image from the primary image of said fundus by the light passing through the opening of said apertured mirror, the improvement residing in that said objective lens has, in succession form the side of said eye, a first group including a biconvex lens having its more curved surface facing said apertured mirror, and a second group including a doublet positive meniscus lens component convex to the eye to be examined whose cemented surface convex to said apertured mirror, the two lens surfaces of said biconvex lens, namely the first surface ($r_1$) and the second surface ($r_2$) counted from the side of the eye, and the convex surface of said doublet positive meniscus lens component facing the eye, namely the third surface ($r_3$) counted from the side of the eye having convergent refractive power, respectively.

2. The optical system according to claim 1, wherein said illuminating optical system further has a first and a second transparent black point plate disposed between said first and said second relay lens, said first and second black point plates have first and second black points, respectively, on the optic axis, said first and second black points are projected onto the vicinity of said objective lens by said second relay lens and said apertured mirror and the images of said first and second black points are formed in such a manner that the image of said first black point is conjugate with the opening of said apertured mirror with respect to the reflected light on the second surface ($r_2$) of said objective lens, of the illuminating light provided by said illuminating optical system and that the image of said second black point is conjugate with the opening of said apertured mirror with respect to the reflected lights on the first surface ($r_1$), the third surface ($r_3$) and the fourth surface ($r_4$) as the cemented surface, of said objective lens, of the illuminating light provided by said illuminating optical system.

3. The optical system according to claim 2, wherein the image of said first black point is formed on that side of the first group of said objective lens which is adjacent to said eye and the image of said second black point is formed within the biconvex lens of the second group of said objective lens.

4. The optical system according to claim 3, wherein the third surface ($r_3$) of said objective lens is an aspherical surface.

5. A fundus observation and photographing optical system having an objective lens for forming a primary image of the fundus of an eye to be examined, an apertured mirror disposed rearwardly of said objective lens and obliquely with respect to the optic axis of said objective lens and having an opening on the optic axis, said mirror being substantially conjugate with the cornea of said eye with respect to said objective lens during the observation or photographing of the fundus, an illuminating optical system having a light source and a first and a second relay lens, said illuminating optical system being adapted to supply illuminating light to said eye via said apertured mirror and through said objective lens, and an image forming relay lens for forming a secondary image from the primary image of said fundus by the light passing through the opening of said apertured mirror, the improvement residing in that said objective lens has, in succession from the side of said eye, a first group including a biconvex lens having first surface ($r_1$) and second surface ($r_2$) as counted from the side of said eye, said first and second surfaces, respectively having convergent refractive power and the second surface being more sharply convex than said first surface, and a second group including a doublet positive meniscus lens component convex to the eye whose cemented surface ($r_4$) convex to said apertured mirror and having foremost convex surface ($r_3$) which has a convergent refractive power and rearmost concave surface ($r_5$) whose center of curvature lies in the vicinity of the opening of said apertured mirror.

6. The optical system according to claim 5, wherein said first and second groups are composed in such a manner that the image position of the opening of said apertured mirror formed by the reflected light on said first surface ($r_1$) of said first group coincides with the image position of the opening of said apertured mirror formed by the reflected light on said cemented surface ($r_4$) of said second group.

7. The optical system according to claim 6, wherein said opening image formed by the light reflected on said first surface ($r_1$) and said opening image formed by the light reflected on said cemented surface ($r_4$) coincide within said biconvex lens of said second group.

8. The optical system according to claim 7, wherein the image of the opening of said apertured mirror formed by the reflected light on said second surface ($r_2$) of said first group is formed at the position between said eye to be examined and said first group.

9. The optical system according to claim 8, wherein said illuminating optical system further has a first and a second transparent black point plate disposed between said first and said second relay lenses, said first and second black point plates have first and second black points, respectively, the image of said first black point is projected on the image position of said opening of said apertured mirror formed by the reflected light on said second surface ($r_2$) of said first group, and the image of said second black point is projected on the image position of said opening of said apertured mirror formed by the reflected light on said first surface ($r_1$).

10. The optical system according to claim 9, wherein the image of said opening of said apertured mirror formed by the reflected light on said foremost convex surface ($r_3$) of said second group and the image of said opening of said apertured mirror formed by the reflected light on said cemented surface ($r_4$) of said second group coincide at the projected image position of said second black point.

11. The optical system according to claim 10, wherein said objective lens satisfies the following conditions:

$$0.7f < |r_2| < 2.0f$$

$$0.6f < |r_3| < 2.0f$$

wherein $r_2$ represents the curvature radius of said second surface of said first group, $r_3$ represents the curvature radius of said foremost convex surface of said second group and f represents the total focal length of the objective lens.

12. The optical system according to claim 11, wherein said objective lens has the numerical data substantially as set forth in the following table:

| | | | | |
|---|---|---|---|---|
| $G_1$ | $r_1 = 380.0$ $r_2 = -38.0$ | $d_1 = 14.0$ $d_2 = 0.5$ | $nd_1 = 1.62041$ | $vd_1 = 60.3$ |
| $G_2$ | $r_3 = 33.8$ $r_4 = -30.0$ $r_5 = 98.5$ | $d_3 = 32.6$ $d_4 = 2.0$ | $nd_2 = 1.62041$ $nd_3 = 1.75520$ | $vd_2 = 60.3$ $vd_3 = 27.5$ |

Total focal length f = 30.5 (unit: mm)

wherein, $r_1$, $r_2$, $r_3$, . . . represent the curvature radii of the respective lens surfaces in succession from the eye to be examined, $d_1$, $d_2$, $d_3$, . . . represent the center thicknesses of and the air spaces between the successive lenses, and nd and vd represent the refractive indices and Abbe numbers, respectively, of the successive lenses.

* * * * *